United States Patent
Richardson et al.

(12) 
(10) Patent No.: US 6,658,876 B1
(45) Date of Patent: Dec. 9, 2003

(54) METHOD AND APPARATUS FOR COLLECTING AND CHILLING WASTEWATER AND LIKE FLUID SAMPLES

(76) Inventors: Michael J. Richardson, 45360 W. Dutch Rd., Franklinton, LA (US) 70438; Hardy C. Richardson, III, 12152 Jim Mizell Rd., Bogalusa, LA (US) 70427

(*) Notice: Subject to any disclaimer, the term of this patent is extended or adjusted under 35 U.S.C. 154(b) by 0 days.

(21) Appl. No.: 10/118,436

(22) Filed: Apr. 8, 2002

Related U.S. Application Data
(60) Provisional application No. 60/363,109, filed on Mar. 11, 2002.

(51) Int. Cl.$^7$ .............................. F25D 17/02; F25D 11/00
(52) U.S. Cl. ............................... 62/201; 62/98; 62/457.2
(58) Field of Search ............................... 62/98, 99, 201, 62/175, 457.2, 457.1; 73/863.11

(56) References Cited

U.S. PATENT DOCUMENTS

| | | | | |
|---|---|---|---|---|
| 2,348,806 A | * | 5/1944 | Gillard et al. .................. 73/21 |
| 3,633,381 A | | 1/1972 | Haaf ........................... 62/222 |
| 3,858,405 A | | 1/1975 | Manzke ........................ 62/196 |
| 3,897,687 A | * | 8/1975 | Burberry ................... 73/422 R |
| 3,950,963 A | | 4/1976 | Sutherland .................... 62/268 |
| 3,959,982 A | | 6/1976 | Denis et al. .................. 62/223 |
| 4,288,996 A | | 9/1981 | Roncaglione ................. 62/384 |
| 4,354,359 A | | 10/1982 | Hall et al. ..................... 62/299 |
| 4,628,748 A | * | 12/1986 | Jogan et al. ............. 73/863.01 |
| 4,637,222 A | | 1/1987 | Fujiwara et al. ............... 62/244 |
| 4,802,338 A | * | 2/1989 | Oswalt et al. .................. 62/98 |
| 5,398,520 A | | 3/1995 | Kamin et al. .................. 62/376 |
| 6,092,381 A | | 7/2000 | Hsiao et al. ................... 62/237 |

* cited by examiner

*Primary Examiner*—Marc Norman
(74) *Attorney, Agent, or Firm*—Garvey, Smith, Nehrbass & Doody, L.L.C.; Charles C. Garvey, Jr.

(57) ABSTRACT

A method and apparatus for collecting and chilling wastewater samples and the like provides an insulated sample container vessel that has cooling coils therein for direct contact and heat transfer with a liquid in the container to rapidly cool the liquid. A refrigeration unit keeps the cooling coils cool. The liquid can be a sample which is required to be stored at 1–3 degrees Centigrade. The chiller is different from similar chillers in that the cooling coils simply are inserted in an insulated container, and can be removed therefrom when it is desired to transport the sample. The sample remains cool during transportation even without the cooling coils. The cooling coils are arranged in the ice chest such that coolant from the chiller enters through the upper coils and exits through the lower coils, causing the liquid sample in the upper part of the container to cool more than the sample in the lower part of the container. The liquid sample drifts down to the bottom, and the warmer sample in the container drifts upwardly, so there is no need for a mechanical stirrer to circulate the sample to make it uniformly cool. The container has a fitting that enables a selected sample to be added to the container interior while the container remains closed.

32 Claims, 5 Drawing Sheets

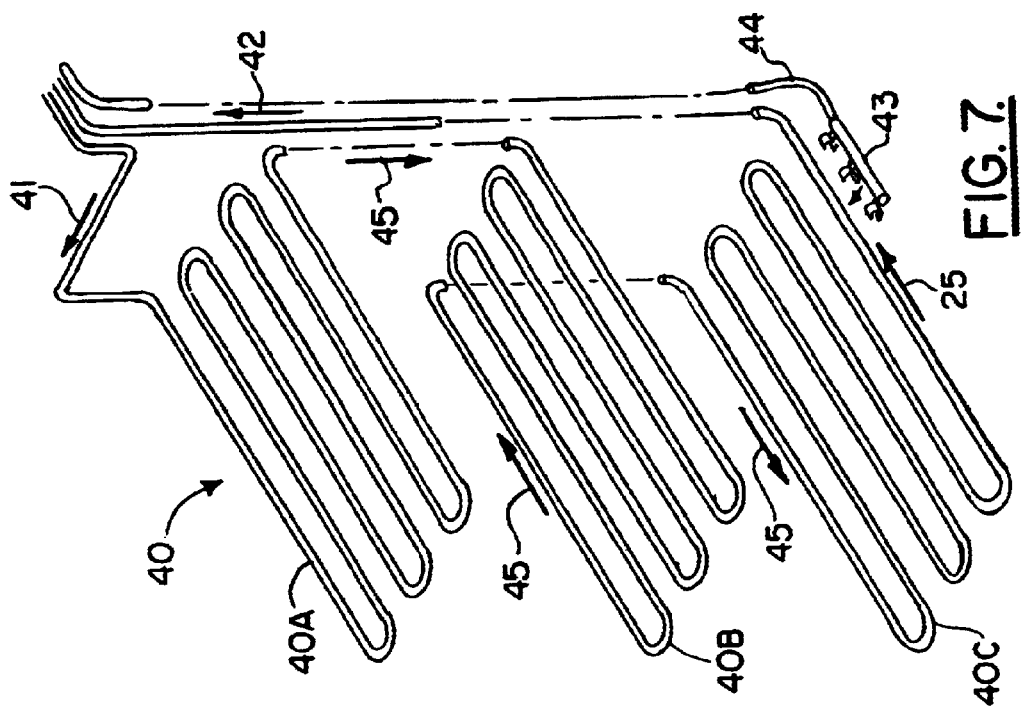
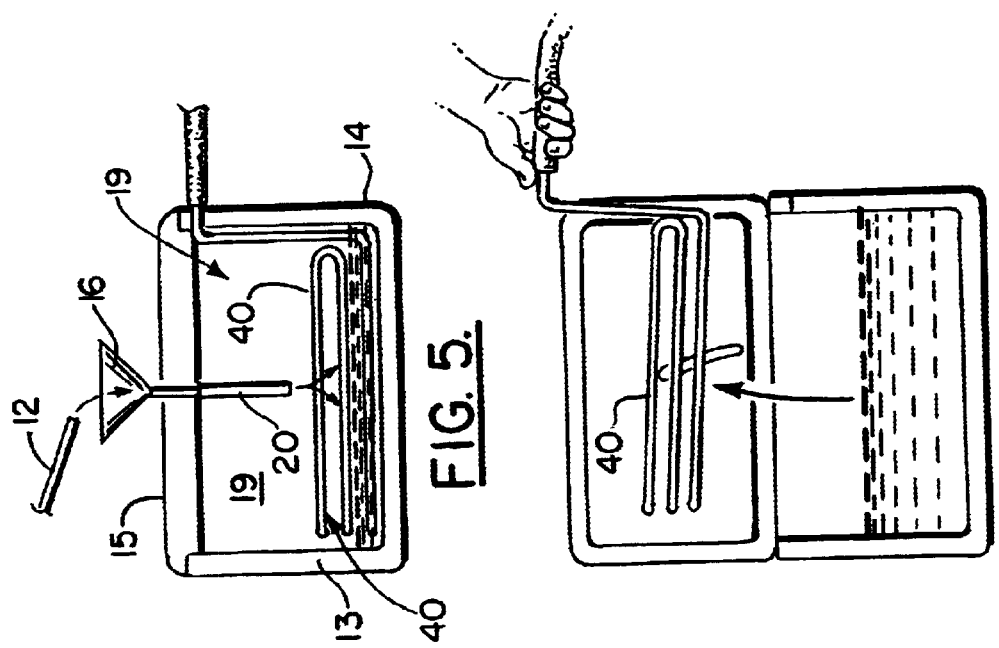

METHOD AND APPARATUS FOR COLLECTING AND CHILLING WASTEWATER AND LIKE FLUID SAMPLES

CROSS-REFERENCE TO RELATED APPLICATIONS

Priority of U.S. Provisional Patent Application Serial No. 60/363,109, filed Mar. 11, 2002, incorporated herein by reference, is hereby claimed.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to collecting and chilling wastewater samples and like fluid samples. More particularly, the present invention relates to an improved method and apparatus for collecting and cooling fluid samples, such as wastewater samples that are collected in a sample container and cooled to a chilled temperature of about one to three degrees centigrade (1–3° C.), the container being a vessel separate from any components of the refrigeration system that might transfer heat to the sample. With the present invention, only coolant filled coil is in contact with the sample. The coolant filled coil is quickly separable from the sample container for transport.

2. General Background of the Invention

The following possibly relevant U.S. Patents are incorporated herein by reference: U.S. Pat. Nos. 3,633,381; 3,858,405; 3,950,963; 3,959,982; 4,288,996; 4,354,359; 4,637,222; 5,398,520 and 6,092,381.

U.S. Pat. No. 6,092,381 discloses supplying a refrigerant line from the outside to cool the interior of a refrigerator box within a vehicle.

U.S. Pat. Nos. 3,633,381 and 3,858,405 disclose refrigerant coils placed in contact of the interior of an ice chest.

U.S. Pat. No. 4,637,222 discloses a refrigerating unit being attached to an ice chest that has coils to accept a refrigerant medium.

U.S. Pat. No. 4,354,359 discloses a refrigerating unit that can be placed within an ice chest to cool the contents.

BRIEF SUMMARY OF THE INVENTION

The present invention comprises a mechanical refrigeration module that has various refrigeration components including a compressor, condenser, and evaporator tank. A closed coolant loop includes the electric pump, a liquid conducting means, an evaporator tank, and a sample container cooling coil.

The electric pump maintains circulation of a selected (e.g. glycol or a glycol water mixture) coolant through a liquid conducting means, the evaporator tank and sample container cooling coil. The electric pump can use a rigid stainless steel pipe section of the liquid conducting means for support. The mechanical refrigeration components, electric pump, and liquid conducting means are mounted on a support frame. The flexible part of the liquid conducting means can be connected to the sample container cooling coil. A standpipe acts as a reservoir for coolant and maintains a selected total dynamic head (TDH) on the suction of the electric pump.

The coolant temperature is maintained at a desired setpoint by means of an electronic temperature control mounted in an electrical control box with a remote sensing probe. The remote sensing probe can be attached to the bottom row of the sample container cooling coil.

The apparatus includes a portable sample container that is preferably insulated and shaped to allow a sample container coil to removably fit inside.

Liquid samples enter the sample container interior via an inlet fitting located on the hinged lid of the sample container. Liquid samples entering the sample container are cooled to the desired temperature range. The actual temperature of the liquid sample can be monitored with a digital thermometer.

The liquid conducting means can include stainless steel piping, a pipe (e.g. PVC) standpipe, and clear flexible (e.g. PVC) tubing.

The present invention provides an improved waste water sample collecting apparatus that includes a refrigeration system having multiple refrigeration components that include at least an evaporator tank, a condenser, a compressor, and an evaporator.

The apparatus includes a sample container vessel that is spaced apart from the refrigeration system components, the sample container vessel having an interior for holding a selected sample of waste water.

A piping system includes flow lines that carry coolant between the refrigeration system and the sample container vessel. The flow lines include a coil mounted in the sample container. The coil conveys coolant to the sample container for enabling heat transfer but not direct contact between the sample in the sample container and the coolant in the coil.

The piping system includes a closed flow line that communicates coolant between the coolant reservoir and the coils in the sample container and a pump for moving fluid in the piping system.

An inlet fitting extends externally of the sample container for enabling a selected waste water sample to be added to the sample container.

A temperature controller controls the temperature of the coil for enabling the temperature of the sample to be lowered to a selected target temperature range via heat transfer with the coil.

The inlet fitting can be in the form of a funnel.

The coolant reservoir can be in the form of a standpipe for supplying a selected pressure head to the pump suction side.

The controller can include a remote sensing probe that is mounted on the coil inside the sample container.

The controller can include a controller box or housing mounted on a first frame that is separate from a second frame that contains the sample container.

The first frame preferably includes the refrigeration system including preferably all of the refrigeration components.

The first frame can include a standpipe for providing a selected pressure head to the suction side of the pump.

The first frame preferably supports a number of refrigeration components including a compressor, condenser, evaporator tank, and pump.

A second frame includes the sample container, sample container cooling coil, inlet fitting, and remote sensing probe.

The present invention also provides an improved method of collecting and chilling waste water samples and the like.

BRIEF DESCRIPTION OF THE SEVERAL VIEWS OF THE DRAWINGS

For a further understanding of the nature, objects, and advantages of the present invention, reference should be had to the following detailed description, read in conjunction with the following drawings, wherein like reference numerals denote like elements and wherein.

Sheet 2 is a partial perspective view of the preferred embodiment of the apparatus of the present invention;

Sheet 3 is partial exploded, perspective view of the preferred embodiment of the apparatus of the present invention;

Sheet 4 is a schematic diagram of the controller circuit for the refrigeration module portion of the preferred embodiment of the apparatus of the present invention;

FIG. 5 is a fragmentary sectional elevation view of the preferred embodiment of the apparatus of the present invention illustrating the sample container portion thereof;

FIG. 6 is a front section elevation view of the sample container of FIG. 5, illustrating removal of the coil so that the sample container can be transported; and FIG. 7 is a fragmentary perspective exploded view of the preferred embodiment of the apparatus of the present invention illustrating the sample container cooling coils.

DETAILED DESCRIPTION OF THE INVENTION

Figure 1:
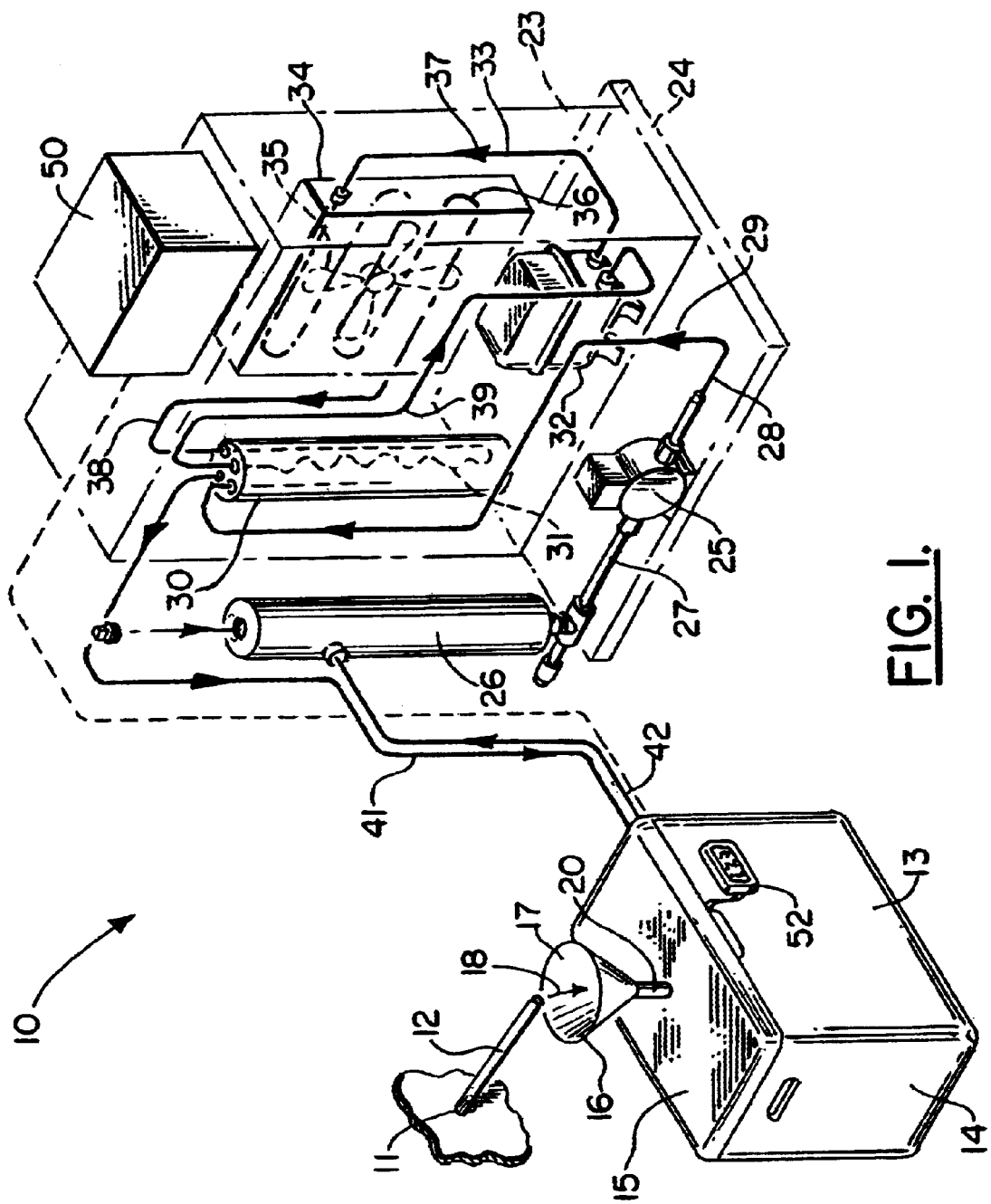
FIG. 1 is a perspective view of the preferred embodiment of the apparatus of the present invention.
Figure 2:
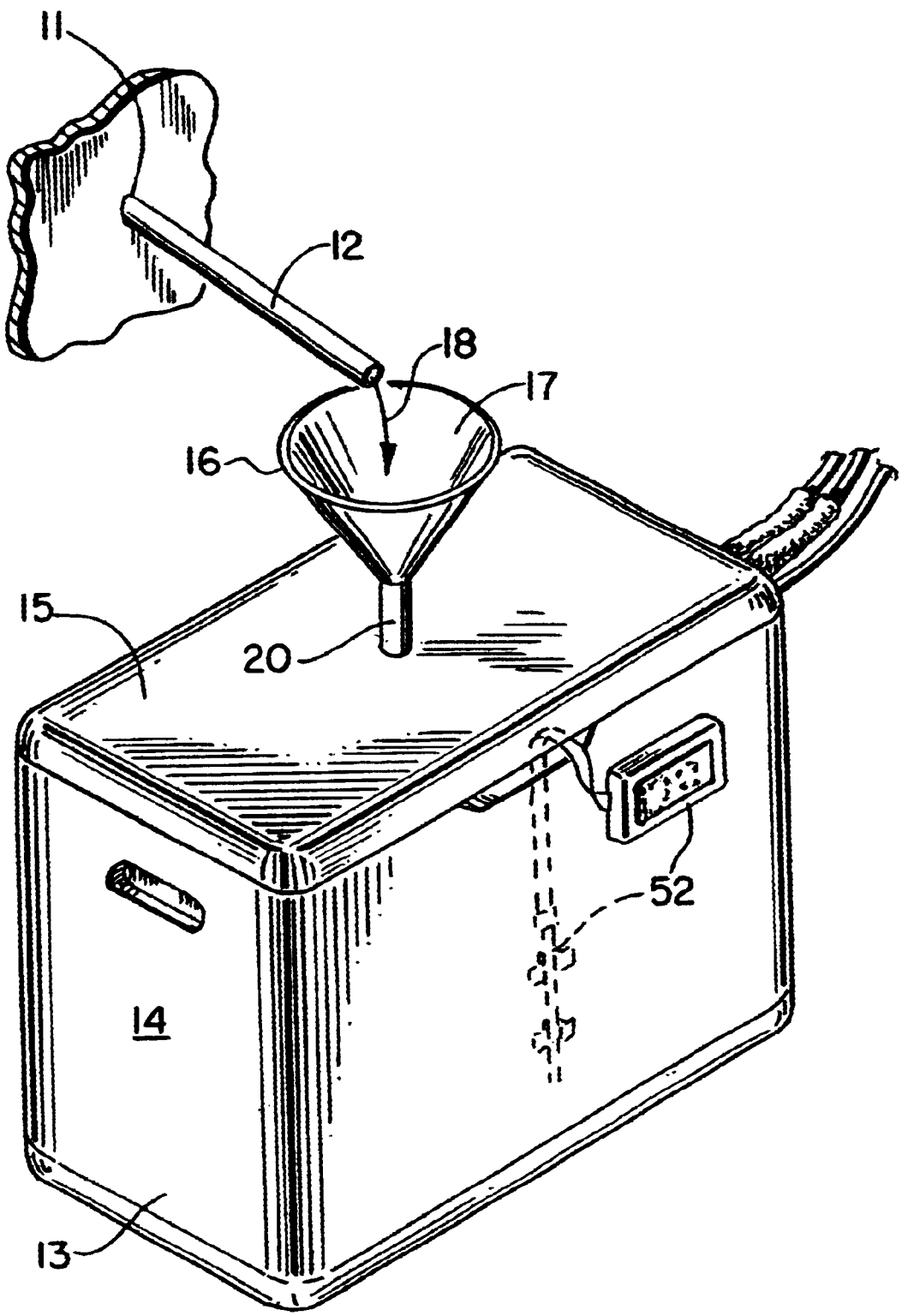

FIGS. 1 and 2 show the preferred embodiment of the apparatus of the present invention designated generally by the numeral 10 in FIG. 1. Sample collecting and chilling apparatus 10 includes a sample container 13 for receiving waste water or like samples from a sample source 11. Sample source 11 can include a conduit 12 that transmits fluid to be sampled to container body 14 and its interior 19.

The container 13 includes a body 14 and cover 15 that preferably removably fits body 14, for closing and sealing the interior 19 such as when a sample that has been collected is to be transported.

Cover 15 has an inlet fitting 16 that helps transmit samples to be collected from a conduit 12 to the container interior 19. Inlet fitting 16 can include a funnel section 17. Arrow 18 in FIGS. 1 and 2 schematically illustrates the transfer of a sample to be collected from conduit 12 to container 13 via inlet fitting 16. The internal temperature of a sample inside Container 13 can be monitored using a digital thermometer 52 as shown in FIGS. 2–3.

The inlet fitting 16 has a flowline section 20 that extends through cover 15 as shown in FIGS. 1, 2 and 5. In this fashion, the inlet fitting 16 communicates with interior 19 of sample container 13. Flowline 20 thus provides an outlet 21 for discharging a collected sample into interior 19 of sample container 13. Cover 15 can be hingedly attached to body 14 for example.

Figure 3:
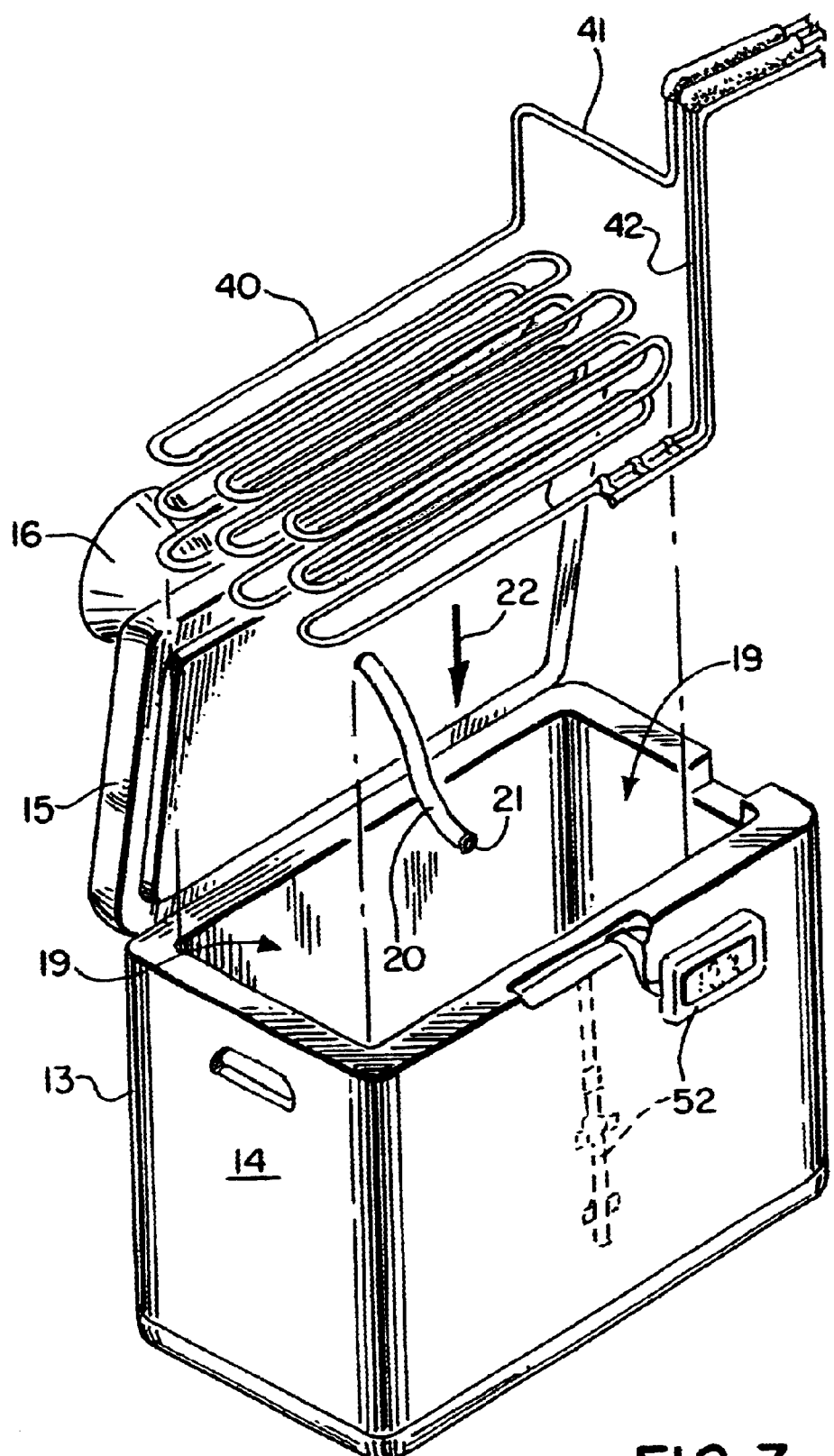

Arrow 22 in FIG. 3 illustrates that a cooling coil 40 can be removably positioned inside of the container 13 as shown in FIGS. 1, 2, 3 and 5–6.

In FIG. 1, a refrigeration module 23 is provided that has a support base 24. It should be understood that this support base 24 is not currently attached to the container 13 so that the sample container 13 can be removed and transported from the overall apparatus 10 once it is filled with a selected volume of a selected sample.

A pump 25 is mounted upon base 24. Standpipe 26 is immediately upstream of pump 25 and provides a selected pressure head to the influent flowline 27 that supplies fluid to the suction side of pump 25. Pump 25 communicates with a discharge flowline 28 that transmits fluid in the direction of arrow 29 to heat exchanger 30.

Heat exchanger 30 has an evaporator coil 31 that is cooled by a number of different refrigeration components that are mounted upon support base 24. These cooling components include compressor 32, discharge flowline 33, condenser 34, fan 35, and condenser coil 36. After being discharged from compressor 32, coolant (for example, R134A coolant) travels in the direction of arrow 37 in flowline 33. Flowline 38 communicates between condenser coil 36 and heat exchanger 30. Return flowline 39 communicates with the influent of compressor 32.

Heat exchanger 30 is filled with a selected coolant such as a mixture (e.g. 50-50) of glycol and water. A closed circuit flow of the glycol water mixture is circulated from heat exchanger 30 via flowline 41 to coil 40 and then through return line 42 to standpipe 26, then to pump 25, and eventually via flowline 28 to heat exchanger 30. There are thus two separate coolant systems. A first coolant system is a refrigerant system using a coolant such as R134A that flows from evaporator coil 31 in heat exchanger 30 to compressor 32 and then to condenser coils 36 and then back to the evaporator coils 31 inside heat exchanger 30. It is the evaporator coil 31 contained inside of heat exchanger 30 that cools the glycol water mixture contained in exchanger 30. The glycol water mixture transmits the very cold glycol water mixture from exchange 30 to coil 40 that is placed inside of the sample container 13 as shown in FIGS. 1, 2,.3, 5–6.

In FIG. 7, the cooling coil 40 includes preferably multiple levels of coils such as the upper level 40A, middle level 40B, and lower level 40C, shown in FIG. 7. The tubing for coil 40 can be ¼" stainless steel coil. Such a stainless material has corrosion resistence to prevent contamination to the waste water samples.

A temperature sensor 43 can be clipped to one of the portions of coil 40 such as the lower section 40c shown in FIG. 7. A control cable 44 communicates between sensor 43 and temperature controller 50 (see FIGS. 4 and 7).

Figure 4:
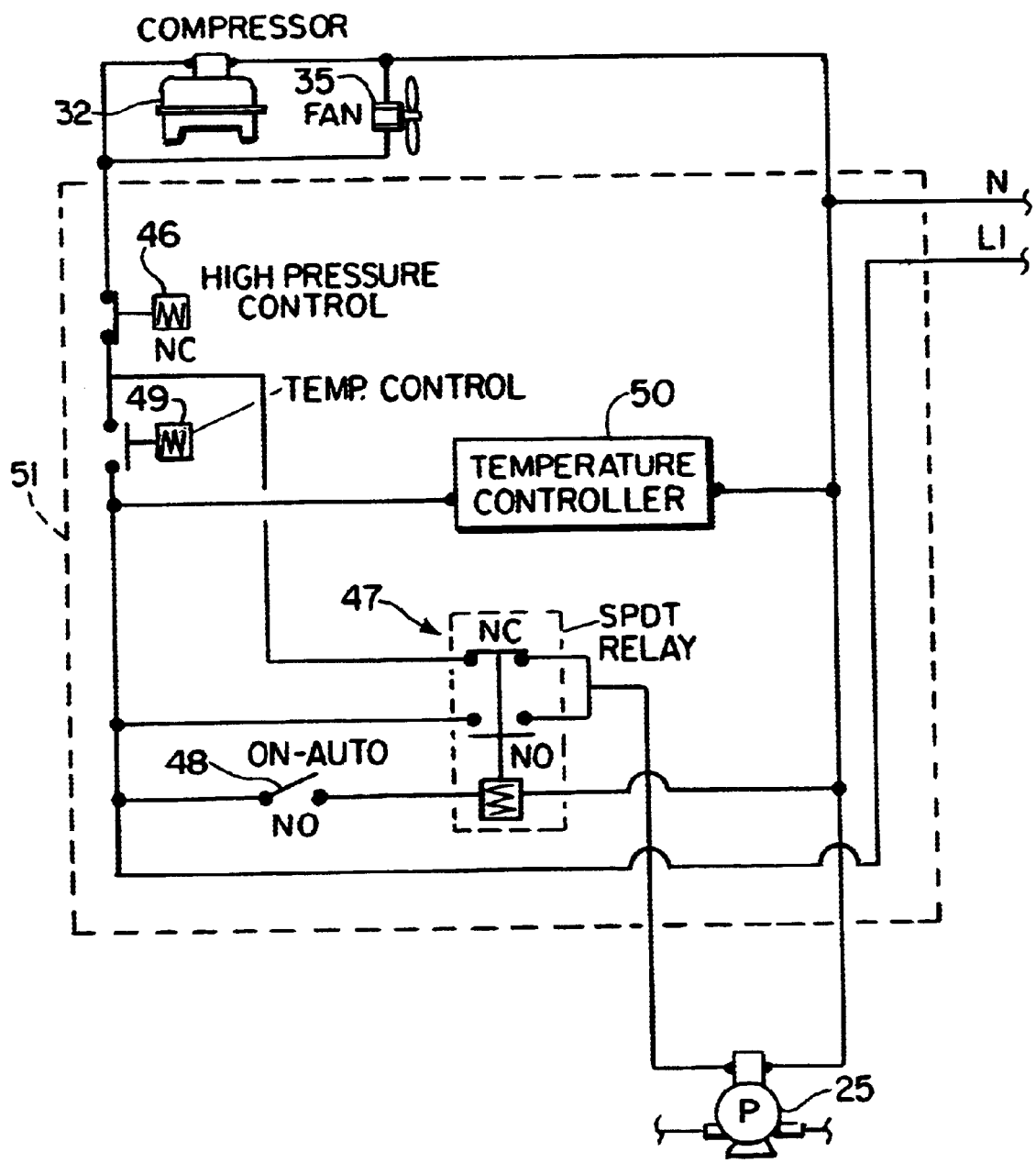

In FIG. 4, there is shown an exemplary electrical schematic for the apparatus 10 of the present invention, the schematic designated by the numeral 51. In FIG. 4, a pressure control switch 46 can be provided for compressor 32 protection in the event of high ambient air temperature or failure of the compressor fan. The electrical system of FIG. 4 can include a 120 volt relay 47 for the pump 25 and an on/off switch 48 for operating the pump relay 47. When the temperature of the fluid sample elevates to a selected preset temperature, the electronic line voltage electronic temperature control 49 has a switch that is activated to turn on the compressor 32 and condenser 34 fan.

During an initial start up, pump switch 48 is placed in an "on" position when purging air from the various flow lines 27, 28, 41, 42 and without running the chiller compressor 32. The apparatus 10 of the present invention seems to operate more efficiently when the pump 25 is run continuously. By running the pump 25 continuously, the mass of the approximate 2¼ gallons of glycol/water solution in the heat exchanger 30 helps keep temperature throughout the entire system consistent and prevents short cycling of the refrigeration compressor 32.

The container 13 having removable coils 40 enables direct contact with the liquid in the container 13 that is being sampled and thus the sample can be rapidly cooled. The refrigeration system maintains the cooling coils 40 at a very cold temperature. The liquid can be sampled and maintained at a required store temperature of about 1–3 degrees centigrade.

The present invention is believed unique in that: 1) the cooling coils 40 are simply inserted into an insulated sample container 13 and can then be quickly removed therefrom when it is desired to transport the sample container 13. Because the sample container 13 is insulated, it remains cool during transportation even without cooling coils 40; 2) the cooling coils 40 are arranged in the sample container 13 such that the coolant from the heat exchanger 30 enters through the upper coils 40A and exits through the lower coils 40C. This causes the liquid sample in the upper part of the interior 19 of container 13 to cool more than the sample in the lower part of the container 13 so that the cooled liquid sample drifts down toward the bottom of the container 13. The warmer sample in the container 13 drifts upwardly. Thus there is no need for a mechanical stirrer to circulate the sample to make it uniformly cool. The high refrigerant pressure switch 46 is not a necessity to the operation of the system 10. It could be advantageous to have as a safety feature.

The apparatus 10 of the present invention is, simply stated, an insulated container 13 with cooling coils 40 therein for direct contact with liquid sample in the container 13 to rapidly cool the selected liquid sample. A refrigeration unit 23 keeps the cooling coils 40 cool. The liquid can be a sample which is required to be stored at 1–3 degrees Centigrade. The range can be, for example, between about 1 and 30 degrees Centigrade, such as around −1 degree Centigrade or around 60 degrees Fahrenheit.

The present invention differs from prior art chillers in that: (a) the cooling coils simply are inserted in an insulated container 13, and can be removed therefrom when it is desired to transport the sample. The sample remains cool during transportation even without the cooling coils 40; and (b) the cooling coils 40 are arranged in container 13 such that coolant from the chiller enters through the upper coils and exits through the lower coils, causing the liquid sample in the upper part of the contanier 13 to cool more than the sample in the lower part of the contanier 13 so the cool liquid sample drifts down to the bottom, of the warmer sample in the container 13 drifts upwardly. There is thus no need for a mechanical stirrer to circulate the sample to make it uniformly cool.

The present invention thus comprises a mechanical refrigeration unit 23 comprising a compressor 32, condenser 34, and evaporator coil 31. A closed coolant loop comprises an electric pump 25, liquid conducting piping 27, 28, 41, 42, standpipe 26, heat exchanger 30, and sample container cooling coil 40. The electric pump 25 maintains circulation of the glycol-water coolant mixture through the liquid conducting flowing 27, 28, 41, 42, the heat exchanger 30 and sample container cooling coil 40. All piping is preferably rigid stainless steel pipe to prevent corrosion.

PARTS LIST

The following is a list of parts and materials suitable for sent invention:
10 sample collecting and chilling apparatus
11 sample source
12 conduit
13 sample container
14 body
15 cover
16 inlet fitting
17 funnel section
18 arrow
19 interior
20 flowline
21 outlet
22 arrow
23 refrigeration module
24 support base
25 pump
26 standpipe
27 inlet flow line
28 discharge flow line
29 arrow
30 heat exchanger
31 evaporator coil
32 compressor
33 discharge flowline
34 condenser
35 fan
36 condenser coil
37 arrow
38 flowline
39 return flowline
40 cooling coil
40A upper level
40B middle level
40C lower level
41 inlet flowline
42 return flowline
43 sensor
44 cable
45 arrow
46 pressure control
47 relay
48 switch
49 temperature control
50 controller housing
51 controller circuit
52 thermometer All mesurements disclosed herein are at standard and pressure, at sea level on Earth, unless indicated otherwise. All materials used or intended to be used in a human being are biocompatible, unless indicated otherwise.

The foregoing embodiments are presented by way of example only; the scope of the present invention is to be limited only by the following claims.

What is claimed is:

1. A wastewater sample collecting apparatus, comprising:
   a) a refrigeration system that includes multiple components including at least an evaporator tank, a condenser, a compressor, an evaporator and a coolant reservoir containing a first coolant fluid;
   b) a sample container vessel that is spaced apart from the refrigeration system components, said sample container vessel having an interior for holding a selected sample of wastewater;
   c) a piping system that includes flowlines that carry a second coolant fluid between the refrigeration system and the sample container vessel, said flowlines including a coil mounted in the sample container, the coil conveying the second coolant to the sample container for enabling heat transfer but not direct contact between the sample in the sample container and the coolant in the coil and wherein the first and second coolants fluids do not mix;

d) wherein the piping system includes a closed flowline that communicates coolant between the coolant reservoir and the coils in the sample container, and a pump for moving fluid in the piping system;

e) an inlet fitting that extends externally of the sample container for enabling a selected wastewater sample to be added to the sample container; and f) a temperature controller that controls the temperature of the coil for enabling the temperature of the sample to be lowered to a selected target temperature range via heat transfer with the coil.

2. The wastewater sample collecting apparatus of claim 1 wherein the inlet fitting is a funnel.

3. The wastewater sample collecting apparatus of claim 1 wherein the coolant reservoir has a standpipe for supplying a selected pressure head to the pump suction side.

4. The wastewater sample collecting apparatus of claim 1 wherein the controller includes a remote sensing probe mounted on the coil inside the sample container.

5. The wastewater sample collecting apparatus of claim 1 wherein the controller is mounted on a first frame that is a separate frame from a second frame that contains the sample container.

6. The wastewater sample collecting apparatus of claim 5 wherein the first frame includes the refrigeration system.

7. The wastewater sample collecting apparatus of claim 5 wherein the first frame includes a standpipe for providing a selected pressure head to the suction side of the pump.

8. The wastewater sample collecting apparatus of claim 5 wherein the first frame supports the compressor, condenser, evaporator tank and pump.

9. The wastewater sample collecting apparatus of claim 5 further comprising a remote sensing probe, and wherein the second frame includes the sample container, sample container cooling coil, inlet fitting, and remote sensing probe.

10. A fluid sample collecting apparatus, comprising:

a) a refrigeration system having multiple components and that include at least a condenser, a compressor, an evaporator tank, and an evaporator mounted upon a common support frame and a liquid refrigerant;

b) a sample container vessel that is spaced apart from the support frame, said sample container vessel having an interior for holding a selected sample of fluid;

c) a piping system that includes a coil mounted in the sample container vessel, the piping system containing and conveying a coolant fluid to the sample container vessel interior for enabling heat transfer but not direct contact between a sample in the sample container vessel and the coolant in the coil;

d) wherein the piping system includes a closed circuit, recirculating flow line that communicates coolant between the support frame and the coils in the sample container vessel;

e) an inlet fitting for enabling a selected wastewater sample to be added to the sample container vessel interior;

f) a temperature controller that controls the temperature of the coil for enabling the temperature of the sample to be lowered to a selected target temperature range; and g) a pump that is part of the piping system and positioned externally of the sample container interior, the pump having a discharge and a suction that intakes coolant during use.

11. The fluid sample collecting apparatus of claim 10 wherein the piping system includes a discharge flowline that connects the pump discharge to the coil and a return flowline that connects the pump suction to the coil.

12. The fluid sample collecting apparatus of claim 10 further comprising a stand pipe that is in fluid communication with the pump at the suction side of the pump.

13. The fluid sample collecting apparatus of claim 12 wherein the pump is mounted in a flowline that connects the stand pipe to the pump and the evaporating tank.

14. The fluid sample collecting apparatus of claim 12 wherein a return flowline of the piping system empties coolant into the stand pipe.

15. The fluid sample collecting apparatus of claim 10 wherein the inlet fitting is mounted in the top of the container.

16. The fluid sample collecting apparatus of claim 10 wherein the inlet fitting is a funnel that is mounted on the outside of the container.

17. The fluid sample collecting apparatus of claim 10 further comprising a remote sensing probe that is mounted inside the sample container vessel.

18. The fluid sample collecting apparatus of claim 17 wherein the remote sensing probe is mounted on the coil that occupies the sample container vessel.

19. The fluid sample collecting apparatus of claim 10 further comprising a controller mounted on the common support frame that controls the temperature of the coil for enabling the temperature of the sample to be lowered to a selected target temperature range via heat transfer with the coil.

20. A wastewater sample collecting apparatus, comprising:

a) a refrigeration system having a refrigerant containing a first piping circuit that includes a compressor, a condenser, and an evaporator;

b) a sample container vessel that is spaced apart from the refrigeration system, said sample container vessel having an interior for holding a selected sample of wastewater;

c) a second piping circuit that includes coils mounted in the sample container, the coils conveying coolant to the sample container for enabling heat transfer between a sample in the sample container and the coils;

d) wherein the second piping circuit includes a closed flowline that communicates coolant between the coolant reservoir and the coils in the sample container;

e) an inlet fitting that extends externally of the sample container for enable a selected wastewater sample to be added to the sample container;

f) a temperature controller that controls the temperature of the coil for enabling the temperature of the sample to be lowered to a selected target temperature range;

g) a pump that is part of the piping system external to the sample container interior and including a suction side that intakes coolant from the coolant reservoir; and h) a heat exchanger vessel that contains the evaporator of the first piping circuit and coolant of the second piping circuit.

21. The wastewater sample collecting apparatus of claim 20 wherein the inlet fitting is a funnel.

22. The wastewater sample collecting apparatus of claim 20 wherein the coolant reservoir has a standpipe for supplying a selected pressure head to the pump suction side.

23. The wastewater sample collecting apparatus of claim 20 wherein the controller includes a remote sensing probe mounted on the coil inside the sample container.

24. The wastewater sample collecting apparatus of claim 20 wherein the controller is mounted on a first frame that is a separate frame from a second frame that contains the sample container.

25. The wastewater sample collecting apparatus of claim 24 wherein the first frame includes the refrigeration system.

26. The wastewater sample collecting apparatus of claim 24 wherein the first frame includes a standpipe for providing a selected pressure head to the suction side of the pump.

27. The wastewater sample collecting apparatus of claim 24 wherein the first frame supports the compressor, condenser, evaporator tank and pump.

28. The wastewater sample collecting apparatus of claim 24 further comprising a remote sensing probe, and wherein the second frame includes the sample container, sample container cooling coil, inlet fitting, and remote sensing probe.

29. A fluid sample collecting apparatus, comprising:
   a) a refrigeration system that includes a compressor, a condenser and an evaporator mounted upon a common support frame, said refrigeration system having a flowing refrigerant;
   b) a sample container vessel that is spaced apart from the support frame, said sample container vessel having an interior for holding a selected sample of fluid;
   c) a piping system that includes coils mounted in the sample container vessel, the piping system conveying a liquid coolant to the sample container vessel interior for enabling heat transfer between a sample in the sample container and the coils;
   d) wherein the piping system includes a closed flow line that communicates coolant between the support frame and the coils in the sample container vessel;
   e) an inlet fitting for enabling a selected wastewater sample to be added to the sample container vessel interior;
   f) a temperature controller that controls the temperature of the coil for enabling the temperature of the sample to be lowered to a selected target temperature range;
   g) a pump that is part of the piping system and positioned externally of the sample container interior, the pump having a suction side that intakes coolant during use; and
   h) a heat exchanger that includes a vessel for contacting coolant with the evaporator.

30. Apparatus for cooling a liquid sample, comprising:
   a) an insulated container;
   b) cooling coils in the insulated container for direct contact with a liquid sample in the insulated container to rapidly cool the liquid sample;
   c) a refrigeration unit for keeping the cooling coils cool; and
   d) wherein the cooling coils include upper coils and lower coils and the insulated container includes an upper part and a lower part, and the cooling coils are arranged in the insulated container such that coolant from the refrigeration unit enters through the upper coils and exits through the lower coils, thus causing the liquid sample in the upper part of the insulated container to cool more than the liquid sample in the lower part of the insulated container, so the cool liquid sample drifts downward, and the warmer sample in the insulated container drifts upwardly, so there is no need for a mechanical stirrer to circulate the liquid sample to make it uniformly cool.

31. The apparatus of claim 30, wherein the liquid sample is required to be stored at 1–3 degrees Centigrade.

32. The apparatus of claim 30, wherein the cooling coils are inserted in the insulated container, and can be removed therefrom when it is desired to transport the liquid sample, thus allowing the liquid sample to remain cool during transportation.

* * * * *